US010285890B1

(12) United States Patent
Pigazzi et al.

(10) Patent No.: US 10,285,890 B1
(45) Date of Patent: *May 14, 2019

(54) METHOD OF SECURING A PATIENT ONTO AN OPERATING TABLE WHEN THE PATIENT IS IN A POSITION SUCH AS THE TRENDELENBURG POSITION AND APPARATUS THEREFOR INCLUDING A KIT

(71) Applicants: Alessio Pigazzi, Mission Viejo, CA (US); Glenn Keilar, Mission Viejo, CA (US)

(72) Inventors: Alessio Pigazzi, Mission Viejo, CA (US); Glenn Keilar, Mission Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/251,710

(22) Filed: Jan. 18, 2019

Related U.S. Application Data

(63) Continuation of application No. 16/232,506, filed on Dec. 26, 2018, which is a continuation of application
(Continued)

(51) Int. Cl.
*A61B 5/00* (2006.01)
*A61F 5/30* (2006.01)
(Continued)

(52) U.S. Cl.
CPC ............ *A61G 13/126* (2013.01); *A61B 5/704* (2013.01); *A61F 5/30* (2013.01); *A61F 5/3769* (2013.01);
(Continued)

(58) Field of Classification Search
CPC .. A61G 99/00; A61G 13/123; A61G 13/1225; A61G 13/1245; A61G 13/127;
(Continued)

(56) References Cited

U.S. PATENT DOCUMENTS 2,764,150 A  9/1956 Ettinger
2,835,902 A  5/1958 Fash
(Continued)

OTHER PUBLICATIONS

Klauschie, Jennifer, et al. "Use of Anti-Skid Material and Patient-Positioning to Prevent Patient Shifting during Robotic-Assisted Gynecologic Procedures" published Jul./Aug. 2010 in the Journal of Minimally Invasive Gynecology, vol. 17 No. 4.
(Continued)

*Primary Examiner* — Tarla R Patel
(74) *Attorney, Agent, or Firm* — Nils H. Ljungman & Associates

(57) ABSTRACT

A method of securing a patient onto an operating table when the patient is in a position such as the trendelenburg position and apparatus therefor including a kit. A viscoelastic pad is used to support and hold a patient on a medical procedure table during a medical procedure performed while the table, and thus the patient lying thereon, is in an inclined position, such as the Trendelenburg position. The viscoelastic pad has characteristics which promote a minimization of pressure forces on the patient's body, as well as promote a secure cushioning and holding of the patient in a desired position on the table, in order to minimize injury to the patient.

4 Claims, 11 Drawing Sheets

Related U.S. Application Data

No. 16/123,468, filed on Sep. 6, 2018, which is a continuation of application No. 15/987,602, filed on May 23, 2018, now Pat. No. 10,098,800, which is a continuation of application No. 15/943,245, filed on Apr. 2, 2018, now Pat. No. 10,045,902, which is a continuation of application No. 15/850,126, filed on Dec. 21, 2017, now Pat. No. 9,949,883, which is a continuation of application No. 14/881,274, filed on Oct. 13, 2015, now Pat. No. 9,931,262, which is a continuation of application No. 13/957,778, filed on Aug. 2, 2013, now Pat. No. 9,161,876, which is a continuation of application No. 13/773,290, filed on Feb. 21, 2013, now Pat. No. 8,511,314, which is a continuation of application No. 13/737,552, filed on Jan. 9, 2013, now Pat. No. 8,464,720, which is a continuation-in-part of application No. 13/346,852, filed on Jan. 10, 2012, now abandoned.

(60) Provisional application No. 61/654,339, filed on Jun. 1, 2012.

(51) Int. Cl.

| | | |
|---|---|---|
| *A61F 5/37* | (2006.01) | |
| *A61G 7/10* | (2006.01) | |
| *A61G 13/00* | (2006.01) | |
| *A61G 13/04* | (2006.01) | |
| *A61G 13/10* | (2006.01) | |
| *A61G 13/12* | (2006.01) | |
| *A61G 99/00* | (2006.01) | |

(52) U.S. Cl.
CPC .............. *A61F 5/3776* (2013.01); *A61G 7/10* (2013.01); *A61G 7/1026* (2013.01); *A61G 13/0036* (2013.01); *A61G 13/04* (2013.01); *A61G 13/107* (2013.01); *A61G 13/108* (2013.01); *A61G 13/121* (2013.01); *A61G 13/122* (2013.01); *A61G 13/123* (2013.01); *A61G 13/127* (2013.01); *A61G 13/1225* (2013.01); *A61G 13/1245* (2013.01); *A61G 99/00* (2013.01); *A61G 13/0009* (2013.01)

(58) Field of Classification Search
CPC .. A61G 13/108; A61G 13/121; A61G 13/122; A61G 7/1026; A61G 13/04; A61G 13/0009
USPC ........... 297/284.1, 284.4, 284, 6; 5/652–654, 5/618, 617, 613, 600, 621, 623; 128/845, 128/846
See application file for complete search history.

(56) References Cited

U.S. PATENT DOCUMENTS

| | | |
|---|---|---|
| 3,227,440 A | 1/1966 | Scott |
| 3,512,190 A | 5/1970 | Buff |
| 3,670,725 A | 6/1972 | Gaylord, Jr. |
| 3,780,387 A | 12/1973 | Propst |
| 4,717,611 A | 1/1988 | Petrella et al. |
| 4,840,362 A | 6/1989 | Bremer et al. |
| 4,989,849 A | 2/1991 | Zupancic et al. |
| 5,015,037 A | 5/1991 | Giblin et al. |
| 5,054,142 A | 10/1991 | Owens |
| 5,306,231 A | 4/1994 | Cullum et al. |
| 5,342,278 A | 8/1994 | Dehondt |
| 5,346,378 A | 9/1994 | Dehondt |
| 5,362,302 A | 11/1994 | Jensen et al. |
| 5,402,544 A | 4/1995 | Crawford et al. |
| 5,448,790 A | 9/1995 | Saro et al. |
| 5,661,860 A | 9/1997 | Heitz |
| 5,669,094 A | 9/1997 | Swanson |
| 5,784,734 A | 7/1998 | Scott et al. |
| 5,893,183 A | 4/1999 | Bechtold |
| 6,202,230 B1 | 3/2001 | Borders |
| 6,237,172 B1 | 5/2001 | Morgan |
| 6,401,283 B2 | 6/2002 | Thomas et al. |
| 6,484,334 B1 | 11/2002 | Borders et al. |
| 6,516,483 B1 | 2/2003 | VanSteenburg |
| 6,541,094 B1 | 4/2003 | Landvik et al. |
| 6,568,010 B1 | 5/2003 | Ames |
| 6,620,488 B2 | 9/2003 | Oguri et al. |
| 6,622,727 B2 | 9/2003 | Perry |
| 6,653,363 B1 | 11/2003 | Tursi et al. |
| 6,701,558 B2 | 3/2004 | VanSteenburg |
| 6,754,923 B2 | 6/2004 | Borders et al. |
| 6,772,764 B2 | 8/2004 | Chapman |
| 6,817,363 B2 | 11/2004 | Biondo et al. |
| 6,866,915 B2 | 3/2005 | Landvik |
| 6,904,631 B2 | 6/2005 | Vrzalik et al. |
| 6,924,467 B2 | 8/2005 | Ellis et al. |
| 6,933,469 B2 | 8/2005 | Ellis et al. |
| 7,076,822 B2 | 7/2006 | Pearce |
| 7,189,214 B1 | 3/2007 | Saunders |
| 7,240,384 B2 | 7/2007 | DuDonis |
| 7,441,293 B1 | 10/2008 | Singer et al. |
| 7,552,493 B2 | 6/2009 | McNulty |
| 7,555,794 B2 | 7/2009 | Zelnick et al. |
| 7,603,730 B2 | 10/2009 | Zelnik |
| 7,676,862 B2 | 3/2010 | Poulos et al. |
| 7,731,282 B2 | 6/2010 | Leeds |
| 7,731,283 B2 | 6/2010 | Leeds |
| 7,757,318 B2 | 7/2010 | Poulos et al. |
| 7,789,461 B2 | 9/2010 | Leeds |
| 7,849,540 B2 | 12/2010 | Hill |
| 7,971,298 B2 | 7/2011 | Kobuß et al. |
| 8,011,045 B2 | 9/2011 | Skripps |
| 8,051,513 B2 | 11/2011 | Reed et al. |
| 8,510,885 B2 | 8/2013 | Dennis et al. |
| 8,539,621 B2 | 9/2013 | West |
| 8,856,985 B2 | 10/2014 | Rensink et al. |
| 2004/0016057 A1 | 1/2004 | Traut et al. |
| 2004/0044091 A1 | 3/2004 | Niederoest et al. |
| 2005/0081865 A1 | 4/2005 | Labelle et al. |
| 2005/0210595 A1 | 9/2005 | Di Stasio et al. |
| 2006/0016016 A1 | 1/2006 | Hornbach |
| 2006/0058717 A1 | 3/2006 | Hui |
| 2006/0112490 A1 | 6/2006 | Chausse |
| 2006/0248650 A1 | 11/2006 | Skripps |
| 2008/0010751 A1 | 1/2008 | Kemper et al. |
| 2008/0016618 A1 | 1/2008 | O'Shea et al. |
| 2008/0178390 A1 | 7/2008 | Dudonis |
| 2009/0025150 A1 | 1/2009 | Smalling et al. |
| 2010/0122414 A1 | 5/2010 | Shah |
| 2010/0160470 A1 | 6/2010 | Smiecinski et al. |
| 2010/0212087 A1 | 8/2010 | Leib et al. |
| 2010/0275377 A1 | 11/2010 | West |
| 2010/0281617 A1 | 11/2010 | Brun |
| 2011/0047706 A1 | 3/2011 | Hiebert |
| 2011/0219546 A1 | 9/2011 | West |
| 2013/0289150 A1 | 10/2013 | Hager et al. |

OTHER PUBLICATIONS

"Prevention of Pressure Ulcers in the Surgical Patient", Patina S. et al. Aorn Journal, Mar. 2009, vol. 89, No. 3.
"An Integrative Review of Pressure Relief in Surgical Patients" Armstrong, D. et al, Aorn Journal, Mar. 200, vol. 73, Issue 3.
Meridian Medical, Brochure and Specification Sheet, Surgical Positioners, "Trendelenburg Static Torso Pad", Apr. 3, 2012, 8 pages.
American Chemistry Council, "Diisocyanates Explained" https://dii.americanchemistry.com/Diisocyantes-Explained/.
Merivaara, Practico Operating Table brochure, dated Jan. 2010, 8 pages.
Allen Medical, 2007 catalogue, dated May 24, 2007, 60 pages.
Defloor, Tom et al., "Preventing Pressure Ulcers: An Evaluation of Four Operating-Table Mattresses" Applied Nursing Research, vol. 13, 2000, pp. 134-141.
OR Manager, vol. 24, No. 6, Jun. 2008, 5 pages.

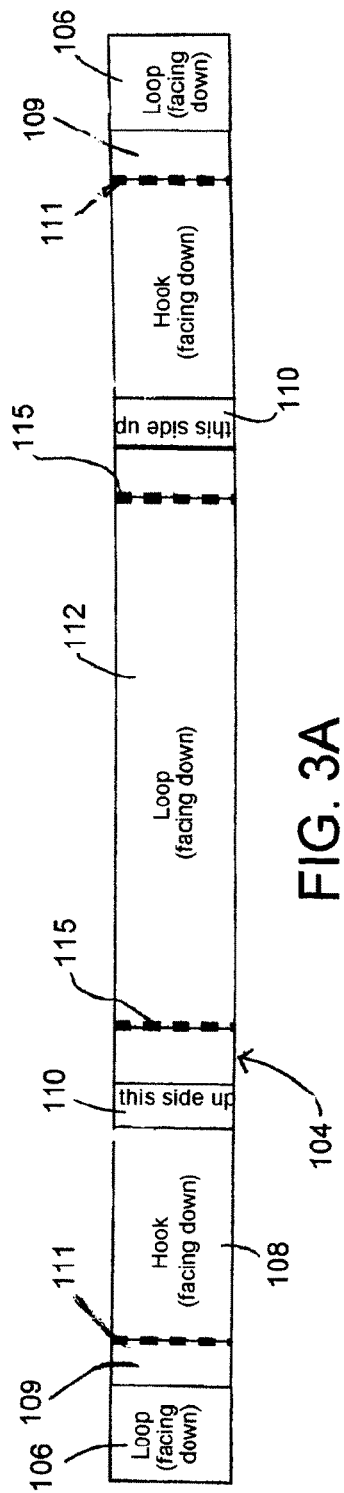
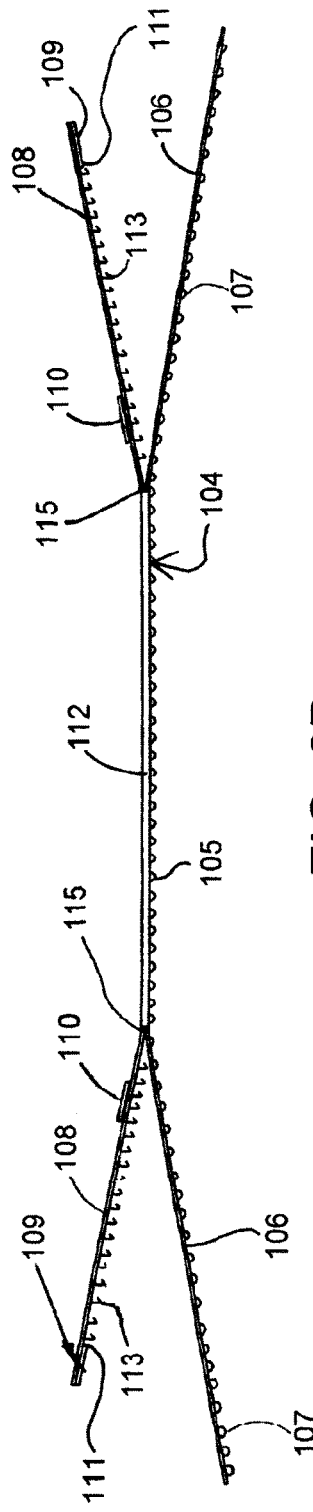

METHOD OF SECURING A PATIENT ONTO AN OPERATING TABLE WHEN THE PATIENT IS IN A POSITION SUCH AS THE TRENDELENBURG POSITION AND APPARATUS THEREFOR INCLUDING A KIT

CONTINUING APPLICATION DATA

The present application is a continuation of U.S. patent application Ser. No. 16/164,420, filed on Oct. 18, 2018, which is a continuation of U.S. patent application Ser. No. 16/123,468, filed on Sep. 6, 2018, which is a continuation of U.S. patent application Ser. No. 15/987,602, filed on May 23, 2018, which is a continuation of U.S. patent application Ser. No. 15/943,245, filed on Apr. 2, 2018, which is a continuation of U.S. patent application Ser. No. 14/881,274, filed Oct. 13, 2015, which is a continuation of U.S. patent application Ser. No. 13/957,778, filed on Aug. 2, 2013, which is a continuation of U.S. patent application Ser. No. 13/773,290, filed on Feb. 21, 2013, which is a continuation of U.S. patent application Ser. No. 13/737,552, filed on Jan. 9, 2013, which is a continuation-in-part of U.S. patent application Ser. No. 13/346,852, filed on Jan. 10, 2012. U.S. patent application Ser. No. 13/773,290 also claims the benefit of U.S. Provisional Patent Application No. 61/654,339, filed on Jun. 1, 2012. U.S. patent application Ser. No. 15/943,245 is also a continuation of U.S. patent application Ser. No. 15/850,126.

BRIEF DESCRIPTION OF THE DRAWINGS

The present application is explained in greater detail below with reference to the accompanying drawings:

FIGS. 3A and 3B show fasteners configured to hold the Trendelenburg pad on the operating table;

DESCRIPTION OF EMBODIMENT OR EMBODIMENTS

During performance of some medical procedures, such as surgical operations, a patient may be placed on a support or operating table which is oriented horizontally, that is, perpendicularly with respect to the vertical. However, depending on the medical procedure, it may be more advantageous to orient the support or operating table, and thus the patient, at an incline with respect to the horizontal. For medical procedures relating to the lower body, such as, for example, abdominal or gynecological operations, the Trendelenburg position may be used. This position involves a patient first lying horizontally on a support table. The operating table or a portion thereof is then inclined such that the head and upper torso of the patient is at a vertically lower position than the pelvic region and/or legs of the patient, as shown, for example, in FIG. 6. In general, the support table is inclined such that the patient's head and upper torso is lowered from the horizontal anywhere in a range of approximately five, ten, or fifteen degrees to approximately twenty, thirty, or forty-five degrees or more, in a steep Trendelenburg position, in one degree increments or fractions of one degree increments. In addition to the positive Trendelenburg position, there is a negative or reverse Trendelenburg position, where the head and upper torso is at a vertically higher position than the pelvic region and/or legs of the patient. As used herein, the phrase Trendelenburg position should be understood as referring to both positions.

Figure 1:
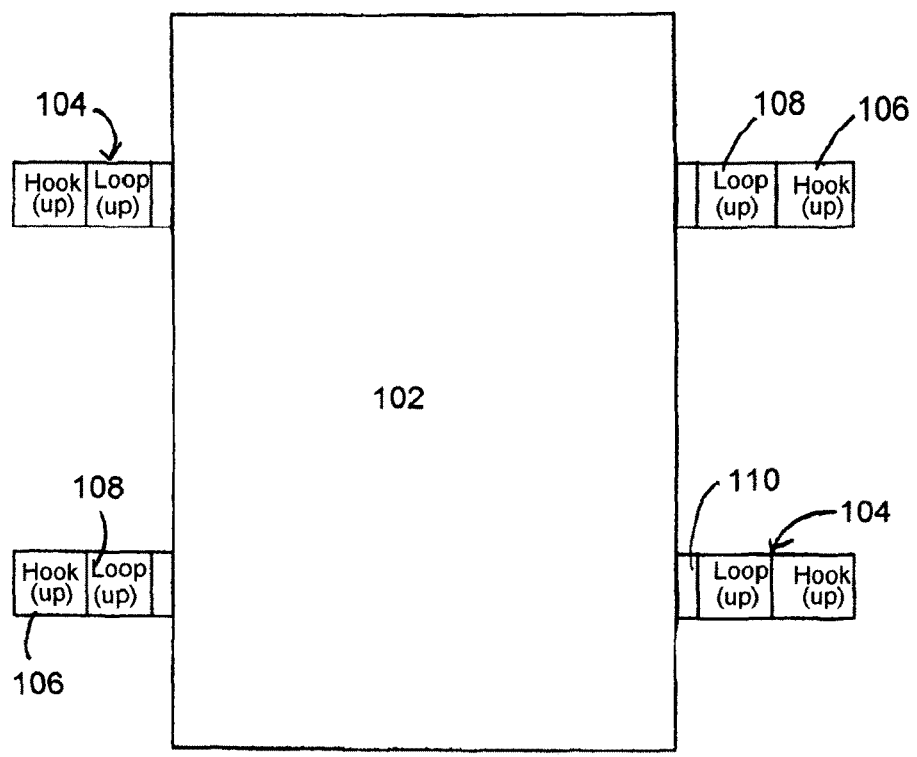
FIG. 1 shows a top view of a Trendelenburg pad of the present application comprising fasteners.

The present application discloses the use of a viscoelastic foam pad, such as shown in FIG. 1, to assist in holding the patient in a desired position on an inclined support table, such as in the Trendelenburg position, and to assist in minimizing sliding, shifting, or similar undesirable movements of the patient on the support table, which movements could be disruptive to a medical procedure being performed on the patient. The viscoelastic foam also cushions and supports the patient while promoting a distribution of pressure forces across the patient's body to reduce and/or minimize damage to nerves and/or tissue from concentrated pressure forces. For example, the viscoelastic foam will minimize or can eliminate brachial plexopathy, including pain, decreased movement, or decreased sensation in the arm and shoulder by minimizing pressure to a patient's neck, arms, and/or shoulders, and thereby minimizing or reducing a nerve event. In at least one possible embodiment, the viscoelastic foam has characteristics which are selected to promote the preceding desired effects, which will be discussed in the following paragraph. All of the characteristics discussed in the following paragraph are according to at least one possible embodiment, and it should be understood that any one or more of the characteristics could be combined with any one or more of the characteristics according to at least one possible embodiment, and any ranges disclosed in the following paragraph are to be understood as including any value therein, including increments of tenths and hundredths of the particular range.

The rate of recovery, that is, the time required for a viscoelastic foam to return to its starting shape, is in the range of approximately 2-10 seconds for approximately 50 percent to 80 percent recovery after deformation caused by placing an adult torso on an approximately one inch thick layer of viscoelastic foam. The rate of recovery is in the range of approximately 6-15 seconds for approximately 80 percent to 90 percent recovery after deformation caused by placing an adult torso on an approximately one inch thick layer of viscoelastic foam. The rate of recovery is in the range of approximately 10-35 seconds for 100 percent recovery after deformation caused by placing an adult torso on an approximately one inch thick layer of viscoelastic foam. The ball rebound of the viscoelastic foam is in the range of less than or substantially less than approximately one percent to approximately one percent or several percent, or is in the range of or approximately in the range of 0.1 percent to 1.9 percent, or up to 3 percent or 5 percent, and as much as several percent. The compression set (the residual compression of the foam after twenty-two hours at seventy degrees Celsius) of the viscoelastic foam, for a 25 percent compression of the foam, is in the range of less than one percent or tenths of a percent, such as, for example, less than 0.4 percent or 0.3 percent, to several percent. The compression set of the viscoelastic foam, for a fifty percent compression of the foam, is in the range of less than one percent or tenths of a percent, such as, for example, less than 0.5 percent, to several percent. The indentation force deflection of the viscoelastic foam, at a 25 percent deflection, is in the range of several pounds of force to tens of pounds of force, such as in the range of approximately 10 to approximately 15 pounds, or in the range of approximately 7 to approximately 18 pounds, or is in the range of approximately 12 pounds, such as, for example, 11.7, 11.8, 11.9, 12.0, 12.1, 12.2, 12.3, and 12.4 pounds. The coefficient of static friction between the viscoelastic foam and the surface of a support table is greater than 0.2, or is in the range of approximately 0.2 or 0.5 to approximately 0.7 or 1.0. The viscoelastic foam is designed such that the patient may shift on the viscoelastic foam less than one inch, or up to approximately an inch, or in the range of approximately one inch to approximately three inches. The airflow in or through the viscoelastic foam is in the range of tenths of a cubic foot per minute to several cubic feet per minute, such as, for example, approximately 0.1 or 0.3 cubic foot per minute to approximately 1.0 or 3.0 cubic feet per minute, or is in the range of approximately 0.53 cubic feet per minute, plus or minus 0.3 cubic feet per minute. The thickness of the viscoelastic foam is in the range of from three-fourths of an inch to one inch, or to approximately one inch, or to one and a half inches, or to three inches or greater, which thickness is selected to minimize and/or prevent bottoming out on the operating table of one or more of the portions of the body of a patient lying on the viscoelastic foam pad, depending on the weight and/or size of the patient. The tensile strength (at 25 percent deflection) of the viscoelastic foam is in the range of at least approximately 5 pounds per square inch (PSI) or approximately 8 PSI to approximately 12 PSI or approximately 15 PSI, or is in the range of approximately 10 PSI. The tear strength (in a twenty inches per minute test) of the viscoelastic foam is in the range of approximately one to approximately two or three pounds of force per inch, or in the range of approximately 1.5 pounds of force per inch. The elongation (in a twenty inches per minute test) of the viscoelastic foam is in the range of between 125 and 250 percent, or is in the range of approximately 172 percent, plus or minus 25 percent. The nominal density of the viscoelastic foam is in a range of approximately 100 kilograms per cubic meter, or is in the range of approximately 75 or 83 kilograms per cubic meter to approximately 103 or 110 kilograms per cubic meter, such as, for example, 93.1 kilograms per cubic meter. The flammability of the viscoelastic foam should pass various tests by CAL, FMVSS and FAR, and the viscoelastic foam should pass the European Union's Restriction of Hazardous Substances (EU RoHS) standards.

According to at least one possible embodiment, the viscoelastic foam pad can be of varying lengths, and can extend from either the feet, lower legs, thighs, or buttocks of a patient to either the shoulders, head, or top of the head of a patient. According to at least one possible embodiment, the viscoelastic foam pad or substantial portions thereof are pink in color, the straps for securing the patient to the pad are purple in color, and the straps for securing the pad to the table or surface are white.

As shown in FIG. 1, a Trendelenburg pad 102 may comprise fasteners 104 extending beyond longitudinal sides of the Trendelenburg pad 102. Each end of the fasteners 104 may comprise a hook and loop fastener, such as a Velcro® fastener, configured and disposed to attach the Trendelenburg pad 102 to operating table rails or other adjacent structures, depending on the support structure on which the patient is positioned, which may or may not be an operating bed. For example, each end of a fastener 104 may comprise a loop portion 108 and a hook portion 106, extending beyond the loop portion 108. Additionally, one or more portions of the fasteners 104 extending beyond the Trendelenburg pad 102 may comprise a label 110 indicating the orientation that the Trendelenburg pad 102 is to have with an operating table. For example, the label 110 may state "this side up."

In at least one possible embodiment of the present application, the Trendelenburg pad 102 may be a disposable pad and/or single-use pad.

Figure 2:
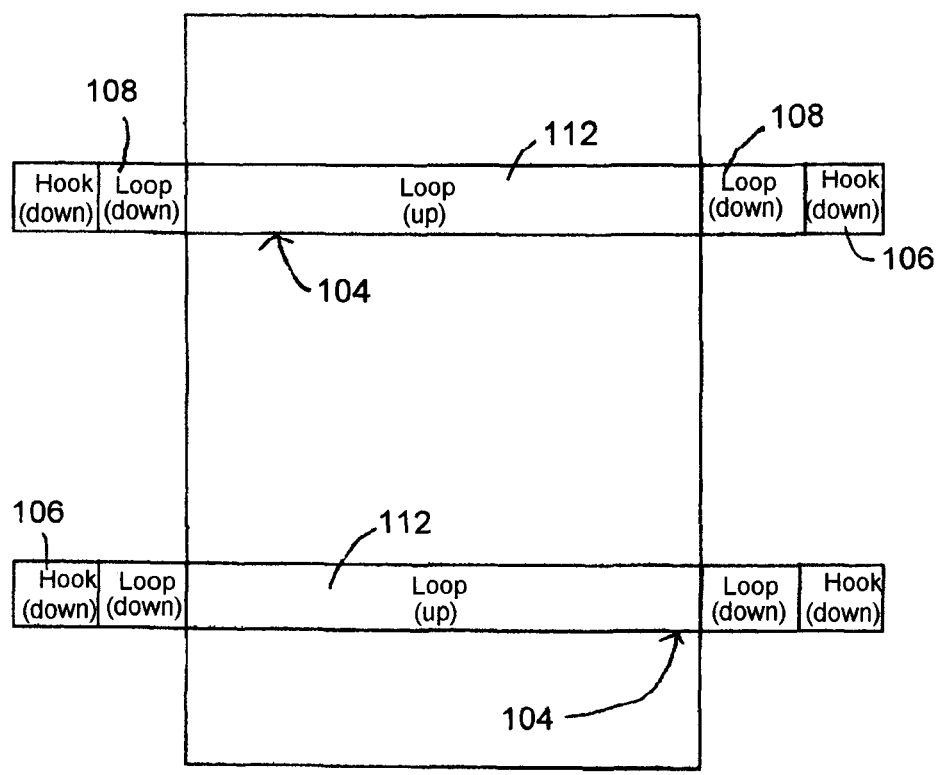
FIG. 2 shows a bottom view of the Trendelenburg pad as seen in FIG. 1.

FIG. 2 shows a bottom view of a Trendelenburg pad 102 comprising fasteners 104 extending latitudinally therewith. A central portion 112 of the fasteners 104 may be configured to be fastened with the Trendelenburg pad 102. For example, the central portion 112 may comprise hooks configured and disposed to fasten with loops on the Trendelenburg pad 102. The Trendelenburg pad 102 may be configured to fasten with two or more fasteners 104. The fasteners may be Velcro®.

FIGS. 3A and 3B show a top view and a side view of a fastener 104 respectively. A central portion 112 of fastener 104 may comprise loops on a side configured to fasten with hooks on a Trendelenburg pad 102 as shown in FIG. 2. A weld 115 may secure a hook portion 108 and a loop portion 106 to the central portion 112 wherein the ends of fastener 104 comprises a hook portion 108 and a loop portion 106. It is to be understood that either portion 108 or 106 may comprise hooks and the other of 108 or 106 may comprise loops. A label 110 may be secured to an upper side of hook portion 108. An end of the hook portion 108 may be folded and welded at a weld point 111 to form a tab 109. Hooks 113 may extend from a lower surface of the hook portion 108. Loops 107 may extend from a lower surface of the loop portion 106.

Figure 4:
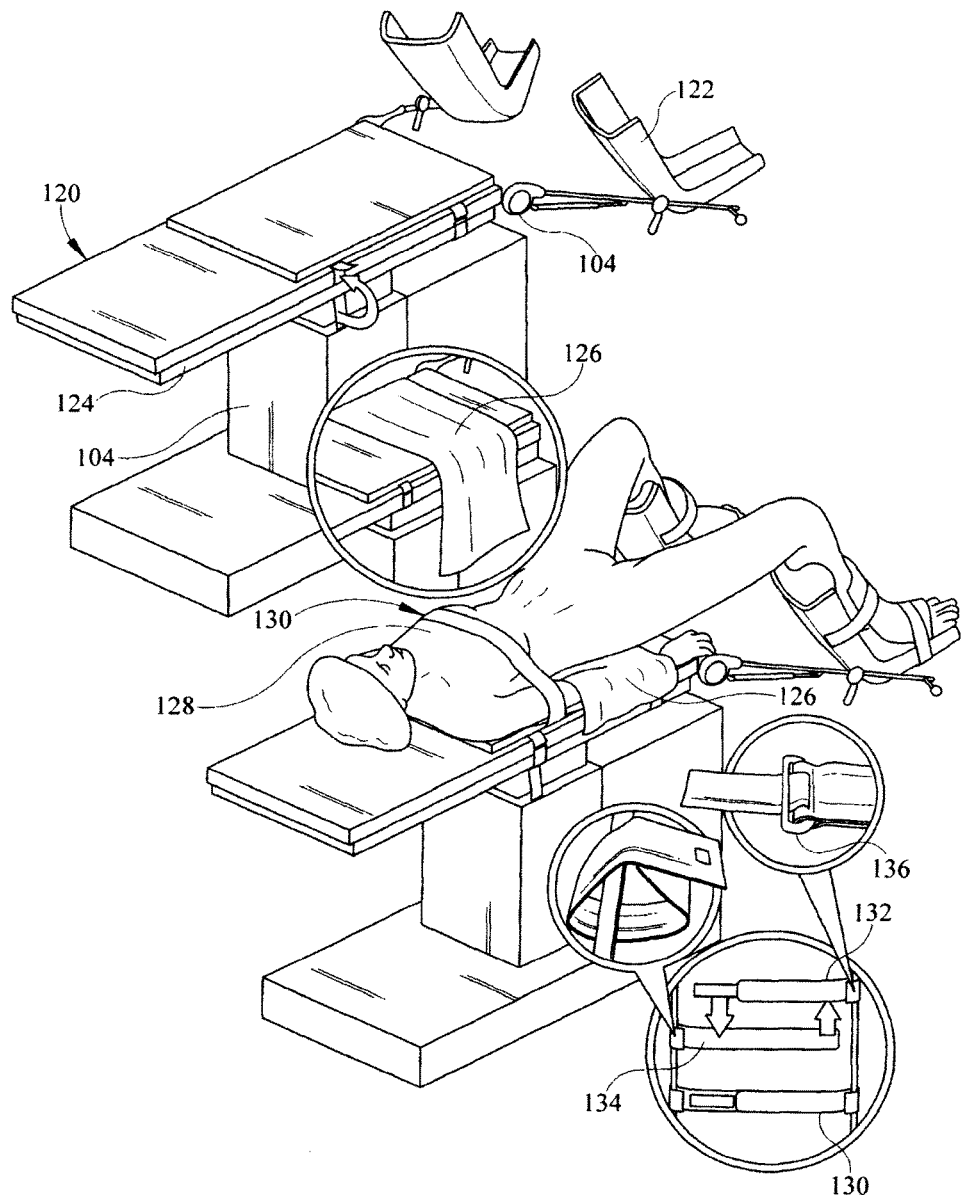
FIG. 4 shows a Trendelenburg pad of the present disclosure secured to an operating table and having a patient positioned thereon and also shows a method of use.

FIG. 4 shows a use of Trendelenburg pad 102. For example, Trendelenburg pad 102 may be used by:

1. Placing a surgical operating table 120, having surgical operating table rails 124, in a Lithotomy Position.

2. Placing a longitudinal distal end of the Trendelenburg pad 102 on a longitudinal distal end of the surgical operating table 120.

3. Latitudinally centering the Trendelenburg pad 102 with the surgical operating table 120.

4. Positioning straps 104, extending from longitudinal edges of the Trendelenburg pad 102, down away from where a patient 128 will lie.

5. Attaching the straps 104 to the surgical operating table rails 124.

6. Laying a lift sheet 126 over the Trendelenburg pad 102.

7. Laying a patient 128 on the Trendelenburg pad 102 by positioning the patient 128 so that the patient's shoulders do not extend past edges of the Trendelenburg pad 102.

8. Lifting the lift sheet 126 thereby lifting the patient 128 up and off the Trendelenburg pad 102 to reposition the patient 128 as needed.

9. Positioning the patient's arms as needed.

10. Attaching body straps 130 around the patient and the surgical operating table.

11. Securing the patient's legs in stirrups 122.

12. Placing the surgical operating table in the Trendelenburg position.

In at least one possible embodiment of the present application, a patient may be disposed on a Trendelenburg pad 102 such that the patient's skin contacts the Trendelenburg pad 102, for example that the patient's skin contacts the Trendelenburg pad 102 in the patient's sacrum and scapula areas of the body and held by the Trendelenburg pad 102. The lift sheet 126 may be used to lift and reposition the patient without dragging the patient across the Trendelenburg pad.

Also shown in FIG. 4 are body straps 130. The body straps 130 may comprise a hook strap 132 and a loop strap 134, such as a Velcro® strap. Each hook strap 132 and each loop strap 134 may comprise a clasp at one end. A hook strap 132 may be secured to a operating table rail 124 by looping therearound and extending through the clasp. A loop strap 134 may be secured to the other operating table rail 124 by looping therearound and extending through the clasp, or secured by extending the hook strap 132 around or to some other portion of the operating table. The hook strap 132 and the loop strap 134 may be fastened about a patient 128, holding the patient 128 to the Trendelenburg pad 102. It is to be understood that body straps 130 are optional as the Trendelenburg pad 102 may provide adequate support of the patient 128 a on surgical operating table 120.

Figure 5:
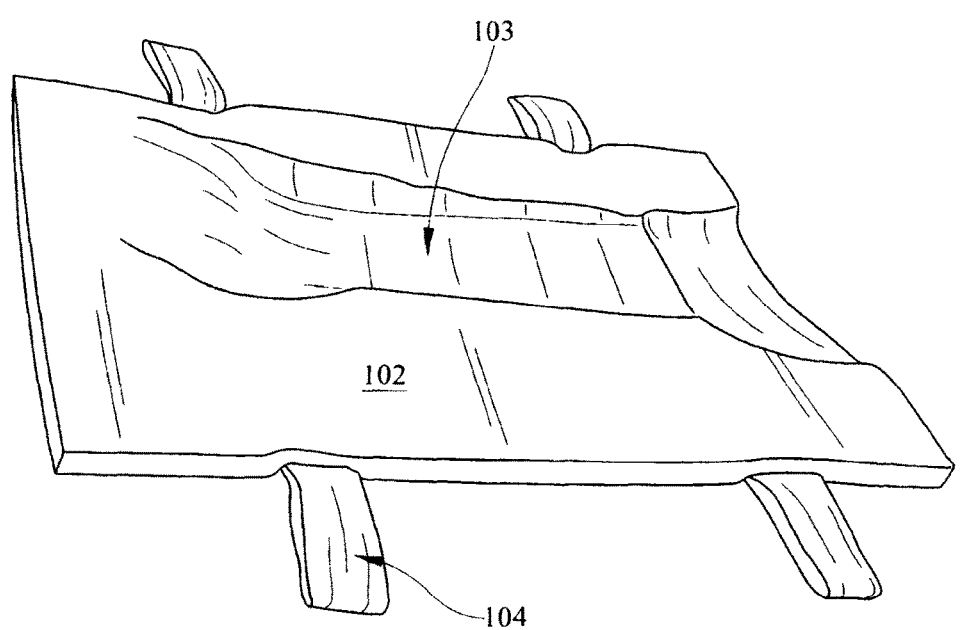
FIG. 5 shows a Trendelenburg pad of the present disclosure having the impression of a patient therein.

FIG. 5 shows a Trendelenburg pad 102 having an impression or residual compression 130 of a patient therein. The Trendelenburg pad 102 comprises viscoelastic foam which conforms to the patient's body and shapes itself to support the body. This shape minimizes pressure points on the body and helps to hold the body on the operating table.

The holding quality or ability between the Trendelenburg Pad and a patient will be a combination of the coefficient of friction between the patient and the viscoelastic foam and the holding ability of the impression made by the patient in the viscoelastic foam, because the Trendelenburg pad is made of a viscoelastic foam in which an impression is formed and held in the foam at least for a time after the patient is moved from one position to another or from the operating table (see FIG. 5). The equivalent total frictional characteristic, which includes the friction due to the coefficient of friction and the friction or friction-like force due to the viscoelastic foam deformation, may be equal to or in excess of one. That is to say, the normal, perpendicular force onto the viscoelastic pad from the body of the patient and component of the force of gravity on the patient parallel to the surface of the operating table at forty-five degrees are equal, which means that the equivalent total frictional characteristic will be equal to or greater than the normal, perpendicular force. For an angle of forty-five degrees, the equivalent total frictional characteristic is one, which is [sin 45°/cos 45°]. Stated more generally, the equivalent total frictional characteristic would be greater than the sine of the angle of inclination from the horizontal over the cosine of the angle of inclination from the horizontal. Since the angle can vary in one degree or smaller increments, the range of values of the equivalent total frictional characteristic could vary between any of those angles so as to be at least or greater than the sine over cosine values of each of these angles of inclination at least within the range of greater than zero degrees to forty-five degrees and also somewhat over forty-five degrees and even greater. The holding capabilities are a combination of the holding ability of the pad, the body straps, and the coefficient of friction of the pad with respect to the patient and the table, between the pad and the sheet between the pad and the patient, and between the sheet and the patient, for all described angles.

Figure 6:
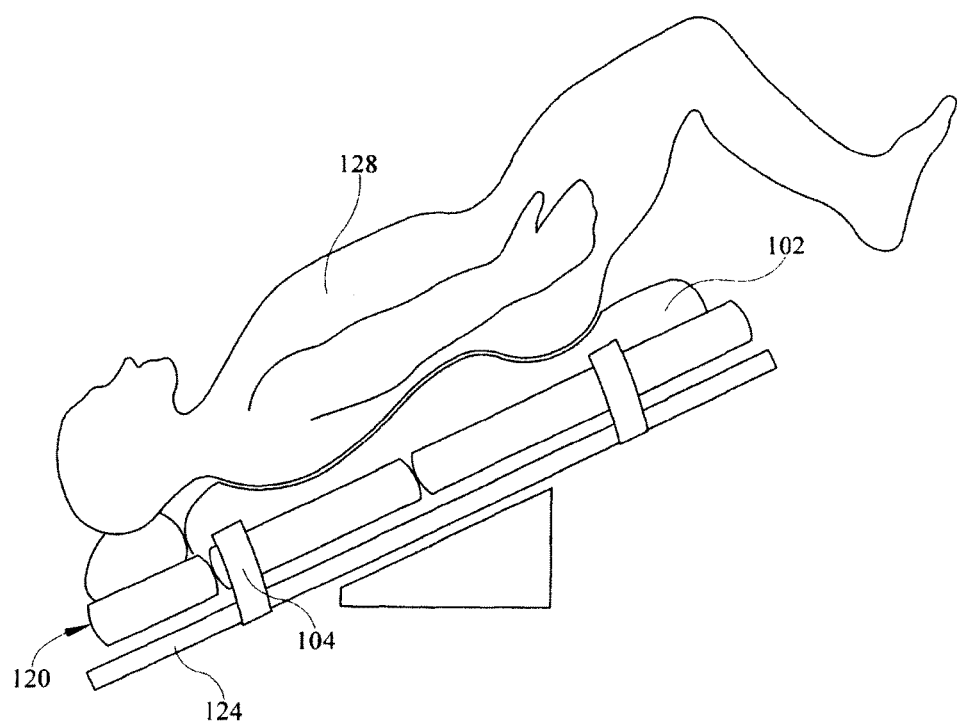
FIG. 6 shows a Trendelenburg pad of the present disclosure secured to an operating table in the Trendelenburg position and having a patient positioned thereon.

FIG. 6 shows a Trendelenburg pad 102 of the present application secured to a surgical operating table 120 with fasteners 104. A patient 128 is positioned on the Trendelenburg pad 102, and the surgical operating table 120 is in the Trendelenburg position. Also shown in FIG. 6 is an aspect of the Trendelenburg pad 102 wherein body straps 130 are not needed to hold a patient 128 on the surgical operating table 120 in the Trendelenburg position.

Figure 7:
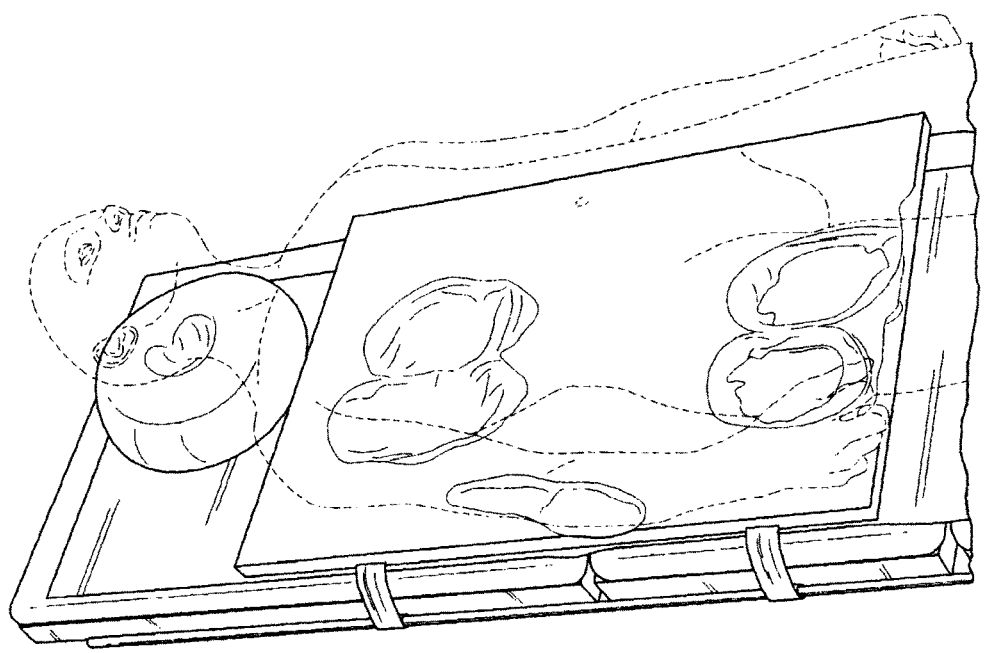
FIG. 7 shows a figure disposed on a Trendelenburg pad of the present application.

FIG. 7 is a computer illustration of a person disposed on a Trendelenburg pad of one possible embodiment of the present application. The figure of the person is transparent or see-through, permitting a view of the impression on the Trendelenburg pad made by the figure of the person. The impression on the Trendelenburg pad may provide the primary holding for holding a person on the operating table depending on the angle of the patient on the table.

Figure 8:
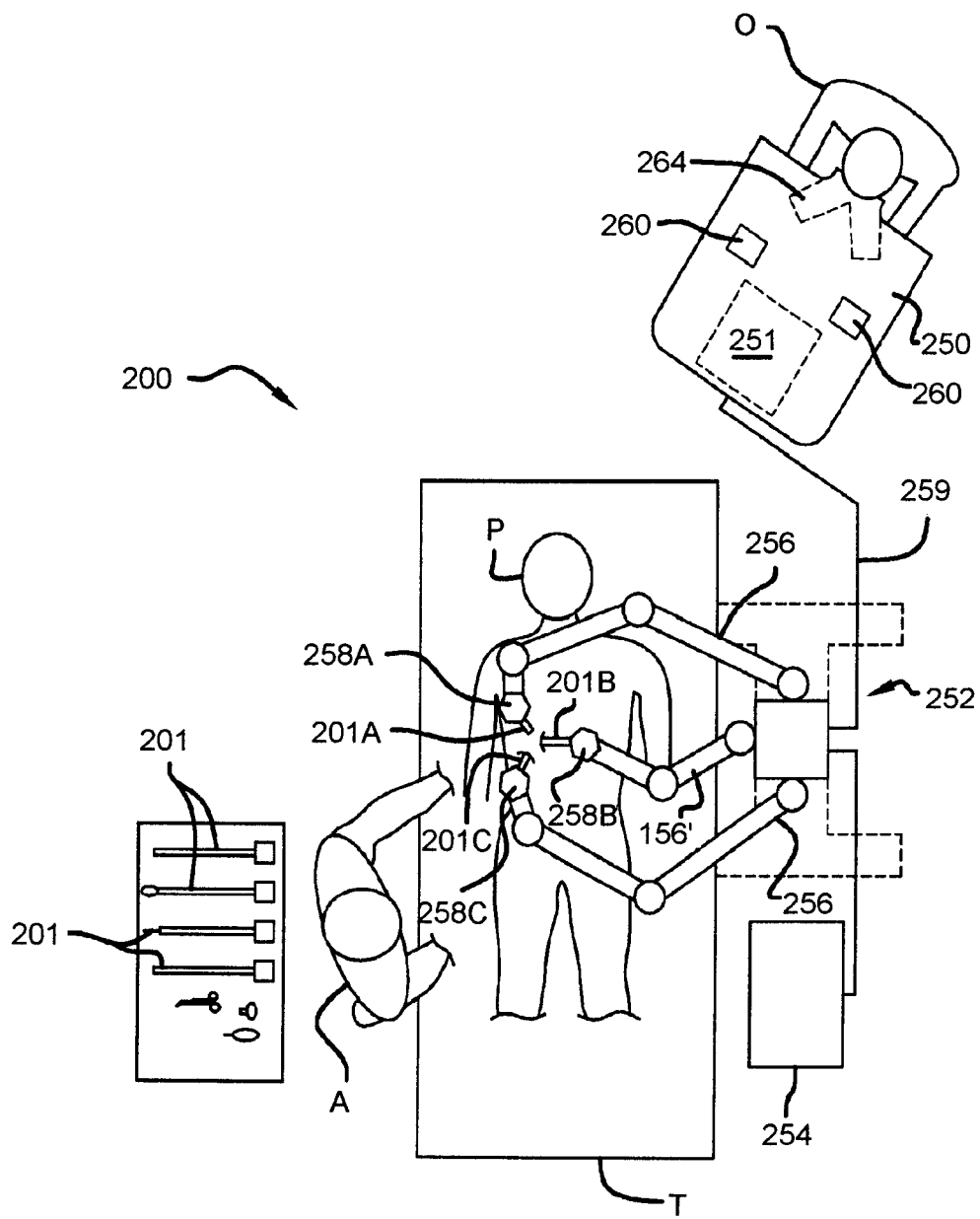
FIG. 8 is a block diagram of a robotic surgery system to perform minimally invasive robotic surgical procedures using one or more robotic surgical arms with a strap drive train.

Referring now to FIG. 8, a block diagram of a robotic surgery system 200 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 258B) is used to support a stereo or three dimensional surgical image capture device 210 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 260 at a master control console 250. A computer 251 of the console 250 directs movement of robotically controlled endoscopic surgical instruments 201A-201C by means of one or more control cables 259, effecting movement of the instruments using a robotic patient-side system 252 (also referred to as a patient-side cart). The robotic patient-side system 252 has one or more robotic arms 258. In one possible embodiment of the Da Vinci Surgical System, the one or more robotic arms 258 have a strap drive system. Typically, the robotic patient-side system 252 includes at least three robotic manipulator arms 258A-258C supported by linkages 256, 256', with a central robotic arm 258B supporting an endoscopic camera 201B and the robotic arms 258A, 258C to left and right of center supporting tissue manipulation tools 201A and 201C.

Generally, the robotic patient-side system 252 includes a positioning portion and a driven portion. The positioning portion of the robotic patient-side system 252 remains in a fixed configuration during surgery while manipulating tissue. The driven portion of the robotic patient-side system 252 is actively articulated under the direction of the operator O generating control signals at the surgeon's console 250 during surgery. The actively driven portion of the robotic patient-side system 252 is generally referred to herein as the robotic arms or alternatively to robotic surgical manipulators. The positioning portion of the robotic patient-side system 252 that is in a fixed configuration during surgery may be referred to as "set up arms" 256, 256' with positioning linkage and/or "set-up joints" (SUJ). In an alternate embodiment of the Da Vinci Surgical System, the robotic patient-side system 252 may be replaced by set up arms that couple at one end to left and right sides of the operating table T. The three robotic manipulator arms 258A-258C may then be coupled to the opposite end of the set-up arms to ground to the table T.

For convenience in terminology, manipulators such as robotic surgical arms 258A and 258C actuating the tissue affecting surgical tools 201A and 201C are generally referred to herein as a PSM (patient-side manipulators), and a robotic surgical arm 258B controlling an image capture or data acquisition device, such as the endoscopic camera 201B, is generally referred to herein as a ECM (endoscope-camera manipulator), it being noted that such telesurgical robotic manipulators may optionally actuate, maneuver and control a wide variety of instruments, tools and devices useful in surgery. The surgical tools 201A, 201C and endoscopic camera 201B may be generally referred to herein as tools or instruments 201.

An assistant A may assist in pre-positioning of the robotic patient-side system 252 relative to patient P as well as swapping tools or instruments 201 for alternative tool structures, and the like, while viewing the internal surgical site via an assistant's display 254. With the embodiments of the Da Vinci Surgical System, the assistant A may also swap in and out the robotic surgical arms 258A and 258C, as well as the robotic surgical arm 258B, in case one is defective or failing. In other cases, a robotic surgical arm may be swapped out for maintenance, adjustments, or cleaning and then swapped back in by one or more service persons.

Figure 9:
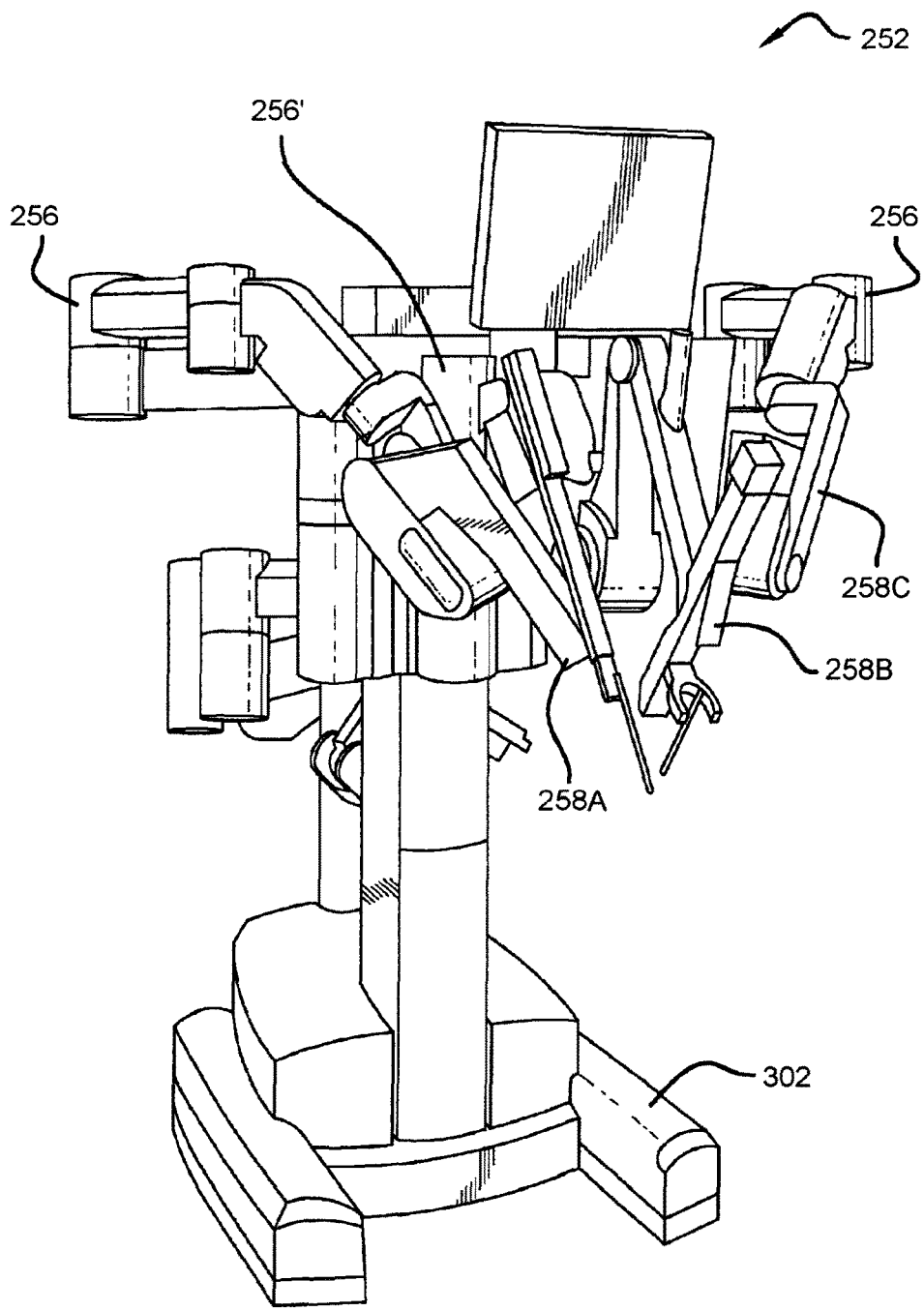
FIG. 9 a perspective view of the robotic patient-side system of FIG. 8 with the one or more robotic surgical arms having the strap drive train.

Referring now to FIG. 9, a perspective view of the robotic patient-side system 252 is illustrated. The robotic patient-side system 252 may have one or more robotic surgical arms (a.k.a., robotic surgical manipulators) 258A-258C with a strap drive system. The robotic arms 258A, 258C are for coupling to robotic surgical tools 201A, 201C. The robotic arm 258B is for coupling to an endoscopic camera 201B. Generally, the surgical robotic arms 258A-258C may be referred to as a surgical robotic arm or a robotic surgical arm 258.

The robotic patient-side system 252 further includes a base 302 from which the robotic surgical instruments 201 may be supported. In at least one possible embodiment of the Da Vinci Surgical System, the robotic surgical instruments 201 are each supported by the positioning linkage 256 and the surgical robotic arms 258. The linkage structures may optionally be covered by protective covers or not to minimize the inertia that is manipulated by the servomechanism and the overall weight of robotic patient-side system 252.

The robotic patient-side system 252 generally has dimensions suitable for transporting between operating rooms. It typically can fit through standard operating room doors and onto standard hospital elevators. The robotic patient-side system 252 may have a weight and a wheel (or other transportation) system that allows the cart to be positioned adjacent to an operating table by a single attendant. The robotic patient-side system 252 may be sufficiently stable during transport to avoid tipping and to easily withstand overturning moments that may be imposed at the ends of the robotic arms during use.

Figure 10:
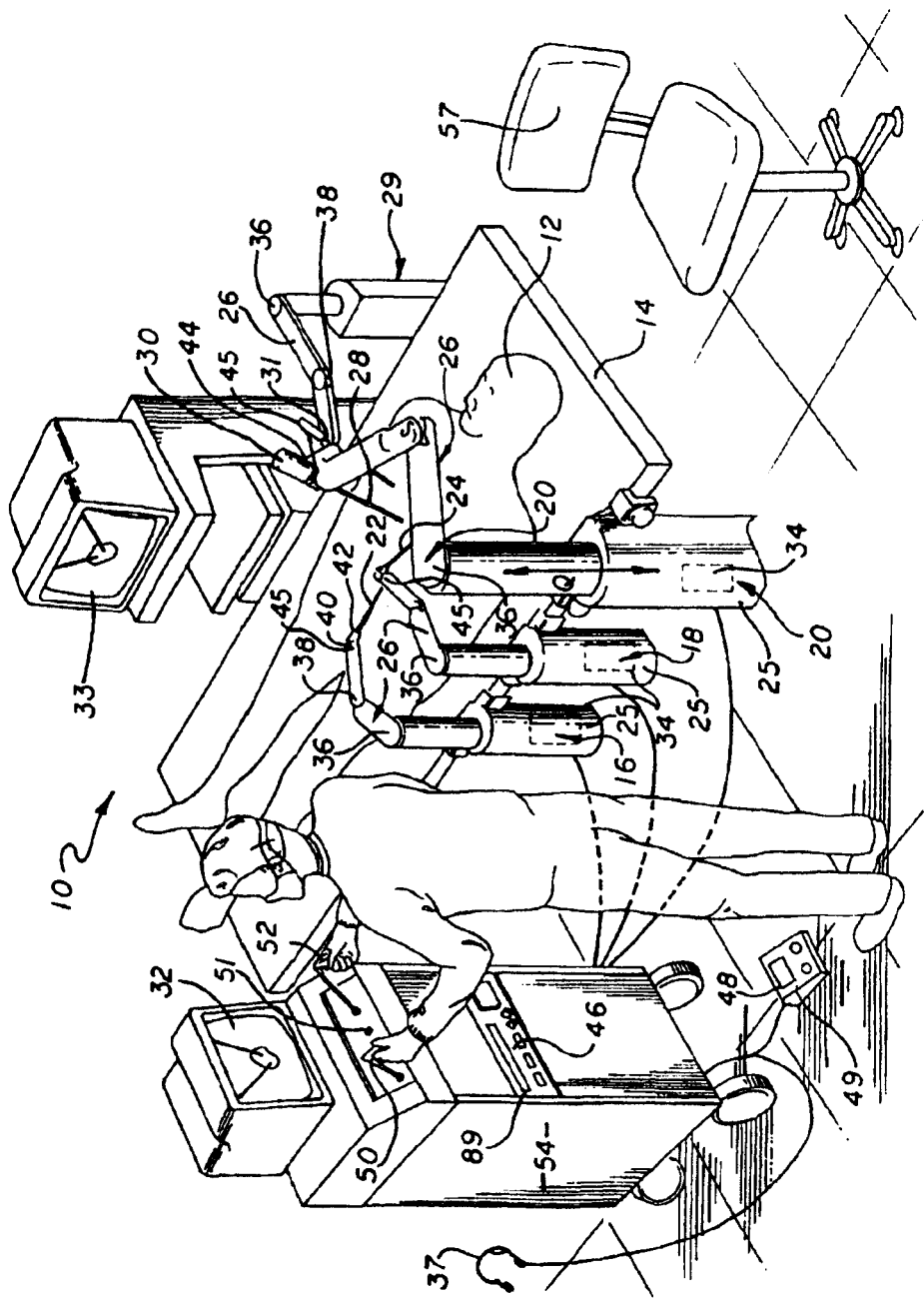
FIG. 10 shows an example of robotic surgery.

FIG. 10 shows an example of a robotic surgery system 10, in which at least one possible embodiment of the Trendelenburg pad could be utilized. In robotic surgery, the consistency of location of the patient is paramount because a shift in position may interfere with the relative positioning of the instruments used in surgery. Due to the ability of the Trendelenburg pad to hold or assist in holding a patient in a desired position, the Trendelenburg pad could be used in robotic surgery. The system 10 may be used to perform a procedure on a patient 12 that is typically lying on an operating table 14. Mounted to the operating table 14 is a first articulate arm 16, a second articulate arm 18 and a third articulate arm 20. The articulate arms 16-20 are mounted to the table so that the arms are in a plane proximate the patient.

The articulate arms 16, 18 and 20 may each comprise a base housing 25 and a robotic arm assembly 26 extending from the base housing 25. Surgical instruments 22 and 24 may be removably coupled at the end of each robotic arm assembly 26 of the first and second articulate arms 16, 18. Each of the instruments 22, 24 may be coupled to a corresponding robotic arm assembly 26.

The third articulate arm 20 may additionally comprise a base housing 25 and a robotic arm assembly 26, and has a first endoscope 28 that is attached to the robotic arm assembly 26. The base housing 25 and robotic arm assemblies 26 of each of the articulate arms 16, 18, and 20 are substantially similar. Additionally, a fourth robotic arm 29 may be included in the system 10. The fourth arm 29 may hold a second endoscope 31.

The instruments 22, 24 and endoscope 28 may be inserted through incisions cut into and through the skin of the patient 12. The first endoscope 28 may comprise a camera 30 that may be coupled to a monitor 32. The monitor 32 may be configured to display images of the internal organs of the patient 12. Additionally, the second endoscope 31 may be inserted through a corresponding incision made in the patient's skin. The second endoscope 31 may be used to provide a wide field of view as depicted in FIG. 10. The second endoscope 31 may be mounted to the fourth robotic arm 29 and may be coupled to a second monitor 33.

Each robotic arm assembly 26 may comprise a base motor 34 which moves the arm assembly 26 in a linear fashion, relative to the base housing 25, as indicated by arrow Q. Each robotic arm assembly 26 may also comprise a first rotary motor 36 and a second rotary motor 38. Each of the robotic arm assemblies 26 may also comprise a pair of passive joints 40 and 42. The passive joints 40, 42 may be disposed orthogonal to each other to provide pivotal movement of the instruments 22, 24 or the endoscopes 28, 31 attached to a corresponding robotic arm assembly 26. The joint angle may be controlled to a particular value using a feedback control loop. The robotic arm assemblies 26 may also comprise a coupling mechanism 45 to couple the instruments 22 and 24, or endoscope 28, 31 thereto. Additionally, each of the robotic arm assemblies 26 may comprise a motor driven worm gear 44 being configured to rotate the instrument 22, 24 or endoscope 28, 31 attached thereto about its longitudinal axis.

The first, second, and third articulate arms 16, 18, 20, as well as the fourth arm 29, may be coupled to a controller 46 which may control the movement of the arms. The arms may be coupled to the controller 46 via wiring, cabling, or via a transmitter/receiver system such that control signals may be passed from the controller 46 to each of the articulate. Each arm 16, 18, 20 and 29 may be electrically connected to the controller 46 via electrical cabling 47.

The controller 46 may be connected to an input device 48 such as a foot pedal, hand controller, or voice recognition unit, to control the position of the endoscope 28 or the second endoscope. To effectuate voice recognition, a microphone 37 is included in the system 10. The controller 46 receives the input signals from the input device 48 and moves the endoscope 28 and robotic arm assembly 26 of the third articulate arm 20 in accordance with the input commands of the surgeon.

The movement and positioning of instruments 22, 24 attached to the first and second articulate arms 16 and 18 is controlled by a surgeon at a pair of master handles 50 and 52. Additionally, a switch 51 may be included in the system 10. The switch 51 may be used by the surgeon to allow positioning of the fourth arm 29. The handles 50 and 52 may be mounted to a portable cabinet 54. A television monitor 56 may be placed onto the cabinet 54 and coupled to the endoscope 28 so that the surgeon can readily view the internal organs of the patient 12. To accommodate a seated position, a chair 57 may be provided with the system.

Figure 11:
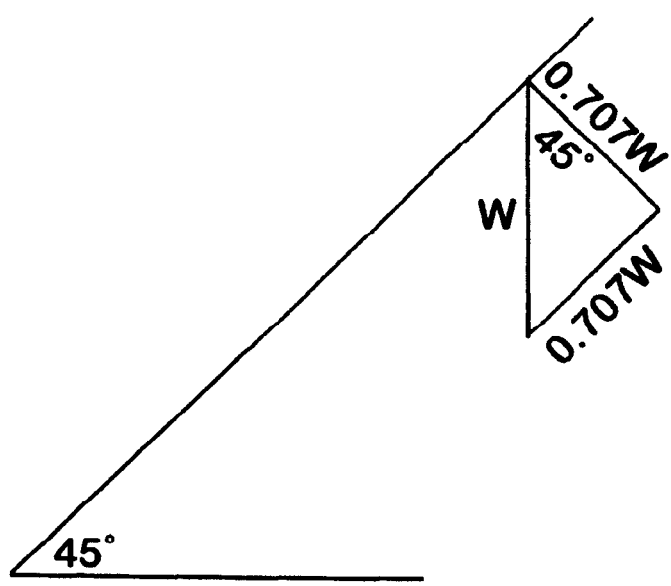
FIG. 11 is a representation of a table inclined at a forty-five degree angle.

FIG. 11 is a representation of a table inclined at a forty-five degree angle. W is the weight of a patient. The normal force perpendicular to the surface of the operating table is 0.707 W. The force along the table is 0.707 W. The equivalent coefficient of friction including the actual coefficient of friction and holding ability of the Trendelenburg pad and the fasteners 130 of the present application to hold a patient is 1.00.

The positioning arrangement and arrangements in the present application could be used in gynecological procedures, colorectal procedures, urological procedures, laparoscopic procedures, and robotic procedures to name some procedures to use this pad in the Trendelenburg or the reverse Trendelenburg position. The positioning arrangement and arrangements, and embodiments of the Trendelenburg pad and kit, in the present application could also be used in all types of medical procedures in which it may be desirable to place a patient in a secure and/or reduced pressure point and/or comfortable position, which medical procedures include surgical procedures and non-surgical procedures, such as non-surgical examinations and/or treatments.

The viscoelastic foam of the present application may be a polyurethane foam made by mixing polyhydroxy polyol with toluene di-isocyanate or other and different methods as are known in the art. For example, Toluene di-isocyanate may be used in combination with polyester polyols and polyether to make viscoelastic foam.

In at least one other aspect of the present disclosure, the Trendelenburg pad 102 is about twenty inches wide, about thirty inches long, and about one inch thick. In one possible embodiment of the present application, the thickness of the pad may be in the range of approximately three-quarters of an inch to approximately one and one-half inches. In that range, the thickness may increase or decrease in increments of 1/32 of an inch. In one possible embodiment of the present application, the width of the pad may be in range of approximately twenty inches to approximately twenty-eight inches. In that range, the width may increase or decrease in increments of one-fourth of an inch or less. In one possible embodiment of the present application, the length of the pad may be in the range of approximately thirty inches to approximately forty inches. In that range, the length may increase or decrease in increments of one-fourth of an inch or less. The fasteners 104 may be Velcro® straps and may be about two inches wide. The fasteners 104 may be secured to the Trendelenburg pad 102 by welding, adhesive, hook and loop fastening, or by other means as is known in the art.

An example of a robotic surgery system, such as the Da Vinci Surgical System, is made by Intuitive Surgical, Inc., located at 1266 Kifer Road #101, Sunnyvale, Calif. 94086.

U.S. Pat. No. 8,066,524, having the title "SURGICAL SYSTEM WITH ELECTRO-MECHANICAL INTERFACES TO MOUNT ROBOTIC SURGICAL ARMS," issued on Nov. 29, 2011, is hereby incorporated by reference as if set forth in its entirety herein except for the exceptions indicated herein.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

One feature or aspect of an embodiment is believed at the time of the filing of this patent application to possibly reside broadly in a method of minimizing injuries caused by pressure on portions of a body of a patient in the Trendelenburg position on a surgical operating table, and minimizing unwanted movement of a patient in the Trendelenburg position on a surgical operating table by securing a patient to the surgical operating table, and also minimizing contamination in an operating room, by using a single-use Trendelenburg patient support system comprising: a lift sheet configured to lift and position a patient on a surgical operating table, body straps configured to hold a patient down on a surgical operating table, a single-use, viscoelastic Trendelenburg pad comprising a rectangular shape and viscoelastic polyurethane, and securing straps welded to said single-use, viscoelastic Trendelenburg pad, which said securing straps are configured to secure said single-use, viscoelastic Trendelenburg pad to rails of a surgical operating table, said method comprising the steps of: A) placing a longitudinal edge of said single-use, viscoelastic Trendelenburg pad adjacent and in alignment with a longitudinal edge of a surgical operating table having surgical operating table rails; B) placing a latitudinal edge of said single-use, viscoelastic Trendelenburg pad adjacent and in alignment with a latitudinal edge of said surgical operating table, and thus positioning said single-use, viscoelastic Trendelenburg pad in a position on said surgical operating table where the body of a patient will be lying; C) positioning said securing straps, extending from longitudinal edges of said single-use, viscoelastic Trendelenburg pad, to extend down and away from said single-use, viscoelastic Trendelenburg pad; D) attaching said securing straps to said surgical operating table rails; E) laying said lift sheet over said single-use, viscoelastic Trendelenburg pad; F) laying a patient in a supine position on said lift sheet and said single-use, viscoelastic Trendelenburg pad by positioning said patient so that the shoulders of said patient do not extend past edges of said single-use, viscoelastic Trendelenburg pad, and thereby deforming said single-use, viscoelastic Trendelenburg pad, which said single-use, viscoelastic Trendelenburg pad comprises: sufficient thickness and viscosity to sufficiently cushion the body of said patient to minimize and/or prevent bottoming out on said medical procedure table of one or more of the portions of the body of said patient during positioning of said patient and during a surgical procedure, and to minimize injuries from pressure during a surgical procedure performed while a patient is in lithotomy and Trendelenburg positions, and sufficient compliance to conform to a substantial portion of the body of said patient; G) lifting said lift sheet and thereby lifting said patient up and off said single-use, viscoelastic Trendelenburg pad to reposition said patient as or if needed; H) positioning the arms of said patient as or if needed; I) attaching said body straps around said patient and said surgical operating table; J) positioning the legs of said patient in a lithotomy position; K) adjusting the angle of inclination of said surgical operating table to orient said patient at an angle in a Trendelenburg position in which the head of said patient is disposed below the body of said patient, or in which the head of said patient is disposed above the body of said patient, or in which the right side of a patient is disposed above the left side or vice versa, or a combination of any of these positions; and L) assisting in substantially holding the body of said patient on said surgical operating table in said lithotomy and Trendelenburg positions using said single-use, viscoelastic Trendelenburg pad, which said single-use, viscoelastic Trendelenburg pad comprises: sufficient thinness to stabilize said patient on said surgical operating table upon said patient being in said lithotomy and Trendelenburg positions, and sufficient thickness and sufficient compliance to permit formation of a cavity in said single-use, viscoelastic Trendelenburg pad of a depth sufficient to assist in holding said patient on said surgical operating table and/or minimizing undesired movement of the body of said patient on said surgical operating table during a surgical procedure performed while said patient is in said lithotomy and Trendelenburg positions.

Another feature or aspect of an embodiment is believed at the time of the filing of this patent application to possibly reside broadly in the method, wherein: said single-use Trendelenburg patient support system comprises a kit; said step D) comprises using securing straps comprising a central portion, attached to a lower side of said single-use, viscoelastic Trendelenburg pad, and fastener ends, each comprising a hook and loop fastener; said single-use, viscoelastic Trendelenburg pad has a thickness in the range of from three-fourths of an inch to three inches or greater; and said single-use, viscoelastic Trendelenburg pad comprises a viscoelastic polyurethane foam having: a ball rebound sufficiently small to minimize rebound of said patient during an operation; a compression set sufficiently small to minimize discomfort of and injury to said patient on said surgical operating table; an air flow sufficient to provide substantial air flow about said patient to minimize injury to said patient and maintain a patient in a useable Trendelenburg position; an indentation force deflection sufficient to provide a securing hold on said patient; a tensile strength sufficient to minimize tearing of said single-use, viscoelastic Trendelenburg pad; a coefficient of static friction sufficient to assist in minimizing movement of said single-use, viscoelastic Trendelenburg pad on said surgical operating table when said patient is on said surgical operating table; and a density configured to provide said ball rebound, said compression set, said air flow, said indentation force deflection, said tensile strength, and said coefficient of static friction.

Yet another feature or aspect of an embodiment is believed at the time of the filing of this patent application to possibly reside broadly in the method, wherein: said single-use, viscoelastic Trendelenburg pad has a thickness of approximately one inch; said ball rebound is in the range of approximately 0.1 percent to approximately 1.9 percent; said compression set, for a 25 percent compression, is less than 0.3 percent; said air flow is in the range of 0.3 to 1.0 cubic foot per minute; said indentation force deflection is in the range of approximately 10 to approximately 15 pounds; said tensile strength is in the range of approximately 8 pounds per square inch to approximately 12 pounds per square inch; said coefficient of static friction is in the range of 0.2 to 1.0; and said density is in the range of approximately 83 kilograms per cubic meter to approximately 103 kilograms per cubic meter.

Still another feature or aspect of an embodiment is believed at the time of the filing of this patent application to possibly reside broadly in a single-use Trendelenburg patient support system for performing the method, said single-use Trendelenburg patient support system comprising: a lift sheet configured to lift and position a patient on a surgical operating table; body straps configured to hold a patient down on a surgical operating table; a single-use, viscoelastic Trendelenburg pad comprising a rectangular shape and viscoelastic polyurethane; securing straps welded to said single-use, viscoelastic Trendelenburg pad; said securing straps being configured to secure said single-use, viscoelastic Trendelenburg pad to rails of a surgical operating table; said single-use, viscoelastic Trendelenburg pad comprising: sufficient thickness and viscosity to sufficiently cushion the body of a patient to minimize and/or prevent bottoming out on said medical procedure table of one or more of the portions of the body of a patient during positioning of a patient and during a surgical procedure, and to minimize injuries from pressure during a surgical procedure; sufficient compliance to conform to a substantial portion of the body of a patient; sufficient thinness to stabilize a patient on said surgical operating table upon a patient being in lithotomy and Trendelenburg positions; and sufficient thickness and sufficient compliance to permit formation of a cavity in said single-use, viscoelastic Trendelenburg pad of a depth sufficient to assist in holding a patient on said surgical operating table and/or minimizing undesired movement of the body of a patient on said surgical operating table during a surgical procedure performed while a patient is in lithotomy and Trendelenburg positions.

A further feature or aspect of an embodiment is believed at the time of the filing of this patent application to possibly reside broadly in the single-use Trendelenburg patient support system, wherein: said single-use Trendelenburg patient support system comprises a kit; said body straps comprise hook and loop fasteners; said securing straps each comprise a central portion, attached to a lower side of said single-use, viscoelastic Trendelenburg pad, and fastener ends, each comprising a hook and loop fastener; said single-use, viscoelastic Trendelenburg pad has a thickness of approximately one inch; and said single-use, viscoelastic Trendelenburg pad comprises a viscoelastic polyurethane having: a ball rebound in the range of approximately 0.1 percent to approximately 1.9 percent; a compression set, for a 25 percent compression, of less than 0.3 percent; an air flow in the range of 0.3 to 1.0 cubic foot per minute; an indentation force deflection in the range of approximately 10 to approximately 15 pounds; a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter.

Another feature or aspect of an embodiment is believed at the time of the filing of this patent application to possibly reside broadly in a method of minimizing injuries caused by pressure on portions of a body of a patient and minimizing unwanted movement of a patient upon securing a patient to a medical procedure table, such as a surgical operating table or a patient examination table, and upon placing said medical procedure table in an inclined position, using a patient support system comprising a viscoelastic pad and securing straps, said method comprising the steps of: A) positioning said viscoelastic pad in a position on said medical procedure table where the body of a patient will be lying; B) attaching said securing straps, connected to said viscoelastic pad, to said medical procedure table; C) positioning a patient on said viscoelastic pad and thereby deforming said viscoelastic pad, which said viscoelastic pad comprises: sufficient thickness and viscosity to sufficiently cushion the body of said patient to minimize and/or prevent bottoming out on said medical procedure table of one or more of the portions of the body of said patient during positioning of said patient and during a medical procedure, and to minimize injuries from pressure during a medical procedure, and sufficient compliance to conform to a substantial portion of the body of said patient; D) adjusting the angle of inclination of said medical procedure table to orient said patient at an angle in an inclined position, in which the head of said patient is disposed below the body of said patient, or in which the head of said patient is disposed above the body of said patient, or in which the right side of a patient is disposed above the left side or vice versa, or a combination of any of these positions; and E) assisting in substantially holding the body of said patient on said medical procedure table using said viscoelastic pad, of which said viscoelastic pad comprises: sufficient thinness to stabilize said patient on said medical procedure table upon said patient being in said inclined position, and sufficient thickness and sufficient compliance to permit formation of a cavity in said viscoelastic pad of a depth sufficient to assist in holding a patient on a medical procedure table and/or minimizing undesired movement of the body of a patient on a medical procedure table during a medical procedure performed while a patient is in an inclined position.

Yet another feature or aspect of an embodiment is believed at the time of the filing of this patent application to possibly reside broadly in the method, wherein: said patient support system further comprises at least one body strap; said patient support system comprises a kit; said method further comprises attaching said at least one body strap around said patient and said medical procedure table between steps C) and D); said step B) comprises using securing straps comprising a central portion, attached to a lower side of said viscoelastic pad, and fastener ends, each comprising a hook and loop fastener; said step D) comprises adjusting the angle of inclination of said medical procedure table to orient said patient in a Trendelenburg position; said viscoelastic pad has a thickness in the range of from three-fourths of an inch to three inches or greater; and said viscoelastic pad comprises a viscoelastic polyurethane foam having: a ball rebound sufficiently small to minimize rebound of said patient during an operation; a compression set sufficiently small to minimize discomfort of and injury to said patient on said medical procedure table; an air flow sufficient to provide substantial air flow about said patient to minimize injury to said patient and maintain a patient in an inclined position; an indentation force deflection sufficient to provide a securing hold on said patient; a tensile strength sufficient to minimize tearing of said viscoelastic pad; a coefficient of static friction sufficient to assist in minimizing movement of said viscoelastic pad on said medical procedure table when said patient is on said medical procedure table; and a density configured to provide said ball rebound, said compression set, said air flow, said indentation force deflection, said tensile strength, and said coefficient of static friction.

Still another feature or aspect of an embodiment is believed at the time of the filing of this patent application to possibly reside broadly in a patient support system for performing the method, said patient support system comprising: a viscoelastic pad; securing straps connected to said viscoelastic pad; said securing straps being configured to secure said viscoelastic pad to a medical procedure table; said viscoelastic pad comprising: sufficient thickness and viscosity to sufficiently cushion the body of a patient to minimize and/or prevent bottoming out on a medical procedure table of one or more of the portions of the body of a patient during positioning of a patient and during a medical procedure, and to minimize injuries from pressure during a medical procedure; sufficient compliance to conform to a substantial portion of the body of a patient; sufficient thinness to stabilize a patient on a medical procedure table upon a patient being in an inclined position; sufficient thinness to stabilize a patient on a medical procedure table upon a patient being in an inclined position, and sufficient thickness and sufficient compliance to permit formation of a cavity in said viscoelastic pad of a depth sufficient to assist in holding a patient on a medical procedure table and/or minimizing undesired movement of the body of a patient on a medical procedure table during a medical procedure performed while a patient is in an inclined position.

A further feature or aspect of an embodiment is believed at the time of the filing of this patent application to possibly reside broadly in the patient support system, wherein: said patient support system further comprises at least one body strap configured to hold a patient down on a medical procedure table while a patient is in a Trendelenburg position; said patient support system comprises a kit; said at least one body strap comprises hook and loop fasteners; said securing straps each comprise a central portion, attached to a lower side of said viscoelastic pad, and fastener ends, each comprising a hook and loop fastener; said viscoelastic pad has a thickness in the range of from three-fourths of an inch to three inches or greater; and said viscoelastic pad comprises a viscoelastic polyurethane foam having: a ball rebound in the range of approximately 0.1 percent to approximately 5 percent; a compression set, for a 25 percent compression, of less than one percent; a air flow in the range of 0.1 to 3.0 cubic foot per minute; a indentation force deflection in the range of approximately 7 to approximately 18 pounds; a tensile strength in the range of approximately 5 pounds per square inch to approximately 15 pounds per square inch; a coefficient of static friction is at least 0.2; and a density in the range of approximately kilograms per cubic meter to approximately 110 kilograms per cubic meter.

Another feature or aspect of an embodiment is believed at the time of the filing of this patent application to possibly reside broadly in a patient support arrangement configured to support and assist in holding a patient on an inclined medical procedure table, said patient support arrangement comprising: a pad comprising a thickness and a viscosity sufficient to cushion the body of a patient to minimize injuries from pressure during a medical procedure, and to minimize and/or prevent bottoming out on a medical procedure table of one or more of the portions of the body of a patient both during positioning of a patient and during a medical procedure; said pad comprising a compliance sufficient to permit said pad to conform to a substantial portion of the body of a patient; said thickness being sufficiently small to stabilize a patient on a medical procedure table upon a patient being in an inclined position; and said thickness and said compliance being sufficient to permit deformation of said pad to a depth sufficient to assist in holding a patient on a medical procedure table, and to assist in minimizing undesired movement of the body of a patient on a medical procedure table, during a medical procedure performed while a patient is in an inclined position.

Yet another feature or aspect of an embodiment is believed at the time of the filing of this patent application to possibly reside broadly in the patient support arrangement, wherein said pad comprises a rebound, such as ball rebound, being sufficiently small to minimize undesirable movement of a patient during a medical procedure.

Still another feature or aspect of an embodiment is believed at the time of the filing of this patent application to possibly reside broadly in the patient support arrangement, wherein said ball rebound is in the range of approximately 0.1 percent to approximately 5 percent.

A further feature or aspect of an embodiment is believed at the time of the filing of this patent application to possibly reside broadly in the patient support arrangement, wherein said ball rebound is in the range of approximately 0.1 percent to approximately 1.9 percent.

One feature or aspect of an embodiment is believed at the time of the filing of this patent application to possibly reside broadly in the patient support arrangement, wherein said pad comprises a compression set being sufficiently small to minimize discomfort of and injury to a patient on a medical procedure table.

Another feature or aspect of an embodiment is believed at the time of the filing of this patent application to possibly reside broadly in the patient support arrangement, wherein said compression set, for a 25 percent compression, is less than one percent.

Yet another feature or aspect of an embodiment is believed at the time of the filing of this patent application to possibly reside broadly in the patient support arrangement, wherein said compression set, for a 25 percent compression, is less than 0.3 percent.

Still another feature or aspect of an embodiment is believed at the time of the filing of this patent application to possibly reside broadly in the patient support arrangement, wherein said pad comprises an indentation force deflection sufficient to provide a securing hold on a patient.

A further feature or aspect of an embodiment is believed at the time of the filing of this patent application to possibly reside broadly in the patient support arrangement, wherein said indentation force deflection is in the range of approximately 7 to approximately 18 pounds.

Another feature or aspect of an embodiment is believed at the time of the filing of this patent application to possibly reside broadly in the patient support arrangement, wherein said indentation force deflection is in the range of approximately 10 to approximately 15 pounds.

Yet another feature or aspect of an embodiment is believed at the time of the filing of this patent application to possibly reside broadly in the patient support arrangement, wherein said pad comprises: a compression set being sufficiently small to minimize discomfort of and injury to a patient on a medical procedure table; and an indentation force deflection sufficient to provide a securing hold on a patient.

Still another feature or aspect of an embodiment is believed at the time of the filing of this patent application to possibly reside broadly in the patient support arrangement, wherein: said pad has a thickness in the range of from three-fourths of an inch to three inches or greater; and said pad comprises: an air flow sufficient to provide substantial air flow about a patient to minimize injury to a patient and maintain a patient in an inclined position; a tensile strength sufficient to minimize tearing of said pad; a coefficient of static friction sufficient to assist in minimizing movement of said pad on a medical procedure table when a patient is on a medical procedure table; and a density configured to provide said ball rebound, said compression set, said air flow, said indentation force deflection, said tensile strength, and said coefficient of static friction.

A further feature or aspect of an embodiment is believed at the time of the filing of this patent application to possibly reside broadly in the patient support arrangement, wherein: said ball rebound is in the range of approximately 0.1 percent to approximately 5 percent; said compression set, for a 25 percent compression, is less than one percent; said air flow is in the range of 0.1 to 3.0 cubic foot per minute; said indentation force deflection is in the range of approximately 7 to approximately 18 pounds; said tensile strength is in the range of approximately 5 pounds per square inch to approximately 15 pounds per square inch; said coefficient of static friction is at least 0.2; and said density is in the range of approximately 75 kilograms per cubic meter to approximately 110 kilograms per cubic meter.

Another feature or aspect of an embodiment is believed at the time of the filing of this patent application to possibly reside broadly in the patient support arrangement, wherein: said ball rebound is in the range of approximately 0.1 percent to approximately 1.9 percent; said compression set, for a 25 percent compression, is less than 0.3 percent; said air flow is in the range of 0.3 to 1.0 cubic foot per minute; said indentation force deflection is in the range of approximately 10 to approximately 15 pounds; said tensile strength is in the range of approximately 8 pounds per square inch to approximately 12 pounds per square inch; said coefficient of static friction is in the range of 0.2 to 1.0; and said density is in the range of approximately 83 kilograms per cubic meter to approximately 103 kilograms per cubic meter.

Yet another feature or aspect of an embodiment is believed at the time of the filing of this patent application to possibly reside broadly in the patient support arrangement, wherein at least one of a)-g): a) said ball rebound is in the range of approximately 0.1 percent to approximately 5 percent; b) said compression set, for a 25 percent compression, is less than one percent; c) said air flow is in the range of 0.1 to 3.0 cubic foot per minute; d) said indentation force deflection is in the range of approximately 7 to approximately pounds; e) said tensile strength is in the range of approximately 5 pounds per square inch to approximately 15 pounds per square inch; f) said coefficient of static friction is at least 0.2; and g) said density is in the range of approximately 75 kilograms per cubic meter to approximately 110 kilograms per cubic meter.

Still another feature or aspect of an embodiment is believed at the time of the filing of this patent application to possibly reside broadly in the patient support arrangement, wherein at least one of h)-n): h) said ball rebound is in the range of approximately 0.1 percent to approximately 1.9 percent; i) said compression set, for a percent compression, is less than 0.3 percent; j) said air flow is in the range of 0.3 to 1.0 cubic foot per minute; k) said indentation force deflection is in the range of approximately 10 to approximately pounds; l) said tensile strength is in the range of approximately 8 pounds per square inch to approximately 12 pounds per square inch; m) said coefficient of static friction is in the range of 0.2 to 1.0; and n) said density is in the range of approximately 83 kilograms per cubic meter to approximately 103 kilograms per cubic meter.

A further feature or aspect of an embodiment is believed at the time of the filing of this patent application to possibly reside broadly in the patient support arrangement, wherein: said pad comprises a viscoelastic material; said patient support arrangement further comprises securing straps attached to said pad and at least one body strap; said securing straps are configured to secure said pad to a medical procedure table; said securing straps each comprise a central portion, attached to a lower side of said pad, and fastener ends, each comprising a hook and loop fastener; said at least one body strap is configured to hold a patient down on a medical procedure table while a patient is in a Trendelenburg position; and said patient support arrangement comprises a kit.

One feature or aspect of an embodiment is believed at the time of the filing of this patent application to possibly reside broadly in a patient support arrangement configured to support and assist in holding a patient in a Trendelenburg position on an inclined medical procedure table, in which the head of the patient is disposed below the body of the patient, or in which the head of the patient is disposed above the body of the patient, or in which the right side of the patient is disposed above the left side or vice versa, or a combination of any of these positions, said patient support arrangement comprising: a pad comprising a viscoelastic polyurethane foam; said pad comprising a thickness and softness sufficient to permit deformation of said pad to a depth sufficient to assist in holding a patient on a medical procedure table during a medical procedure performed while a patient is in a Trendelenburg position; and said pad being configured to recover from a deformation at a rate in a range sufficient to maintain support and minimize disruptive movement of at least a portion of a body of a patient on a medical procedure table during a medical procedure performed while a patient is in a Trendelenburg position.

Another feature or aspect of an embodiment is believed at the time of the filing of this patent application to possibly reside broadly in the patient support arrangement, wherein said rate of recovery of said pad is insufficient to assist in causing disruptive movement of at least a portion of a body of a patient.

The appended drawings in their entirety, including all dimensions, proportions and/or shapes in at least one embodiment of the invention, are accurate and are hereby included by reference into this specification.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A single use Trendelenburg viscoelastic foam pad: configured to minimize injuries on portions of a body of a patient on a medical procedure table, such as a surgical operating table or a patient examination table, said pad comprising a single use pad configured to minimize injuries caused by pressure on portions of a body of a patient and minimize unwanted movement of a patient upon a patient being positioned on a medical procedure table, such as a surgical operating table or a patient examination table, said single use viscoelastic foam pad comprising:

a rate of recovery of said pad in the range of approximately 2 seconds to approximately 35 seconds.

2. A single use Trendelenburg viscoelastic foam pad configured to minimize injuries on portions of a body of a patient on a medical procedure table, such as a surgical operating table or a patient examination table, said pad comprising a single use pad configured to minimize injuries caused by pressure on portions of a body of a patient and minimize unwanted movement of a patient upon a patient being positioned on a medical procedure table, such as a surgical operating table or a patient examination table, said single use viscoelastic foam pad comprising:

an elongation, in a twenty inches per minute test, of the viscoelastic foam in a range of between approximately 125 percent and approximately 250 percent, plus 25 percent or minus 25 percent.

3. A single use Trendelenburg viscoelastic foam pad configured to minimize injuries on portions of a body of a patient on a medical procedure table, such as a surgical operating table or a patient examination table, said pad comprising a single use pad configured to minimize injuries caused by pressure on portions of a body of a patient and minimize unwanted movement of a patient upon a patient being positioned on a medical procedure table, such as a surgical operating table or a patient examination table, said single use viscoelastic foam pad comprising:

a tensile strength, at 25 percent deflection, of the viscoelastic foam in the range of at least approximately 5 pounds per square inch to approximately 15 pounds per square inch.

4. A single use Trendelenburg viscoelastic foam pad configured to minimize injuries on portions of a body of a patient on a medical procedure table, such as a surgical operating table or a patient examination table, said pad comprising a single use pad configured to minimize injuries caused by pressure on portions of a body of a patient and minimize unwanted movement of a patient upon a patient being positioned on a medical procedure table, such as a surgical operating table or a patient examination table, said single use viscoelastic foam pad comprising:

a compression set, for a 25% compression, being less than approximately 0.5 percent.

* * * * *